United States Patent [19]
Martell et al.

[11] Patent Number: 5,316,647
[45] Date of Patent: May 31, 1994

[54] PORTABLE OXYGEN ANALYZER

[75] Inventors: Michael D. Martell, Temecula; Dale A. Conrad, Riverside, both of Calif.

[73] Assignee: Martell Medical Products, Inc., Temecula, Calif.

[21] Appl. No.: 936,107

[22] Filed: Aug. 26, 1992

[51] Int. Cl.$^5$ .................................................. G01N 27/404
[52] U.S. Cl. .................... 204/415; 204/153.1; 204/153.17; 204/400; 204/409
[58] Field of Search .............. 204/153.1, 153.17, 415, 204/431, 432, 400, 409

[56] References Cited

U.S. PATENT DOCUMENTS

| | | | |
|---|---|---|---|
| 2,183,531 | 12/1939 | Allison | 204/420 |
| 3,360,451 | 12/1967 | Stack | 204/415 |
| 3,398,079 | 8/1968 | Arthur et al. | 204/420 |
| 3,424,664 | 1/1969 | Severinghaus | 204/420 |
| 3,434,953 | 3/1969 | Porter et al. | 204/435 |
| 3,878,830 | 4/1975 | Bicher | 204/415 |
| 4,154,660 | 5/1979 | Micko | 204/420 |
| 4,173,975 | 11/1979 | DeLong | 128/142 |
| 4,202,749 | 5/1980 | Phelps et al. | 204/420 |
| 4,269,685 | 5/1981 | Parker | 204/415 |
| 4,280,505 | 7/1981 | Dali et al. | 204/415 |
| 4,367,133 | 1/1983 | Lauer | 204/415 |
| 4,473,458 | 9/1984 | Schwarz et al. | 204/416 |
| 4,577,628 | 3/1986 | Hickmann | 128/205 |
| 4,615,340 | 10/1986 | Cronenberg et al. | 204/415 |
| 4,648,396 | 3/1987 | Raemer | 128/204 |
| 4,779,446 | 10/1988 | Rowland | 73/1 |
| 4,852,563 | 8/1989 | Gross | 128/202 |
| 4,882,576 | 11/1989 | Boyd | 340/632 |
| 4,994,167 | 2/1991 | Shults et al. | 204/415 |
| 4,995,256 | 2/1991 | Norlien et al. | 73/31.04 |
| 4,995,391 | 2/1991 | Jensen et al. | 204/415 |

*Primary Examiner*—T. Tung
*Attorney, Agent, or Firm*—Poms, Smith, Lande & Rose

[57] ABSTRACT

A hand held completely self-contained and shirt pocket size oxygen analyzer for secondary monitoring of oxygen percentage is formed of a housing that contains display and control electronics and a visible display screen. The housing is shaped to form an integral handle and receptacle section for manipulation of a hollow elongated cylindrical configuration having an open end that receives a cylindrical oxygen sensor. The integral cylindrical receptacle section together with the oxygen sensor are arranged to be snugly received in a T-section fitting that is placed in tubing that is connected for inhalation therapy.

7 Claims, 2 Drawing Sheets

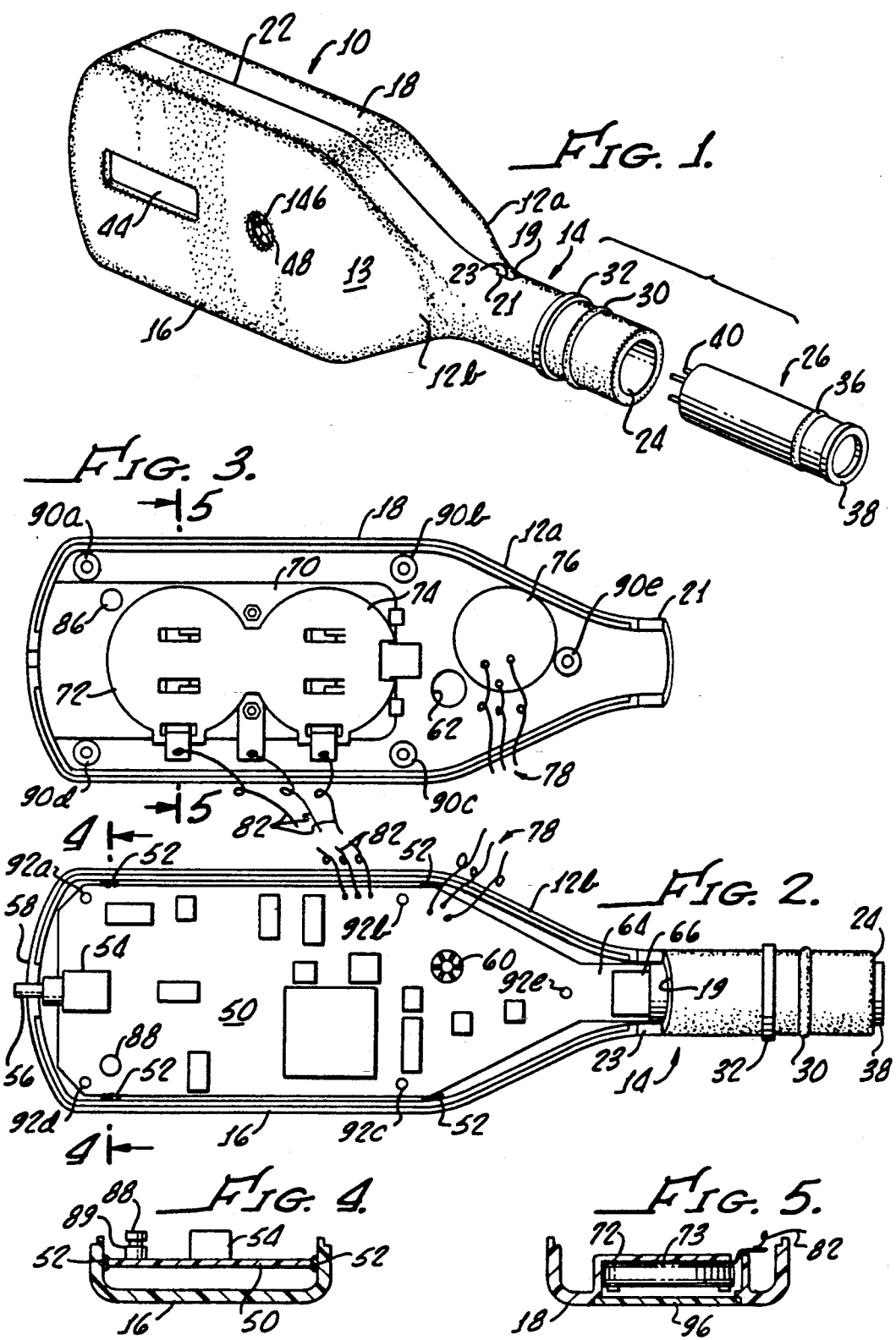

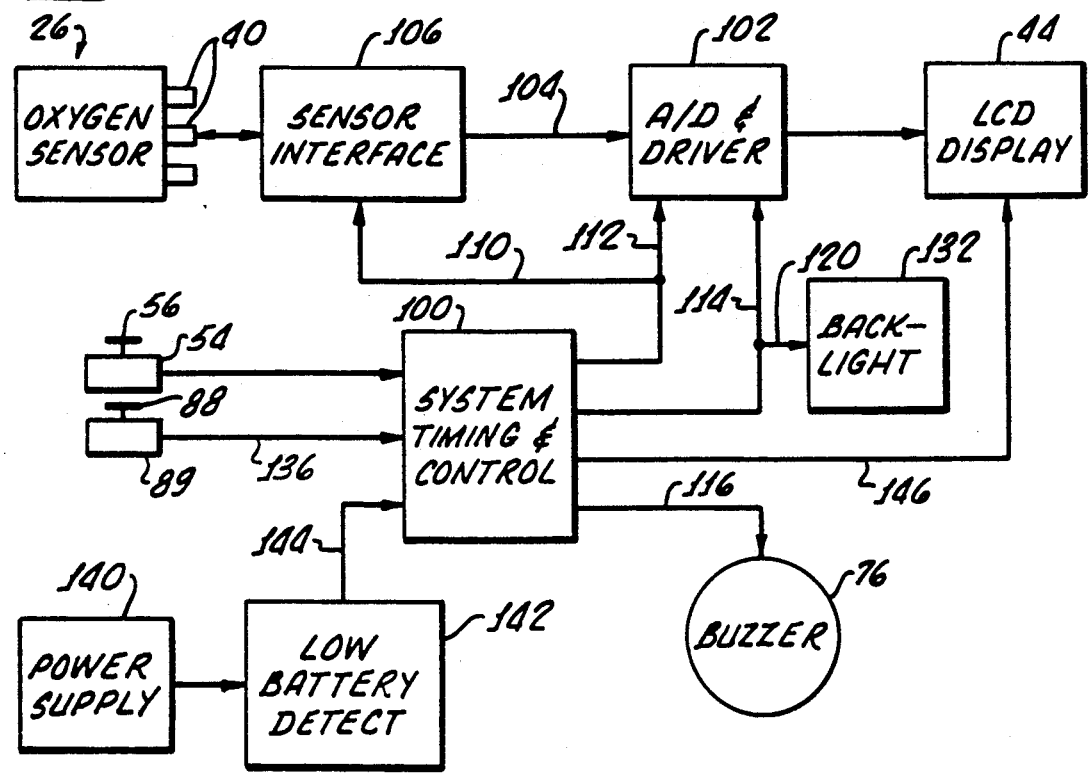
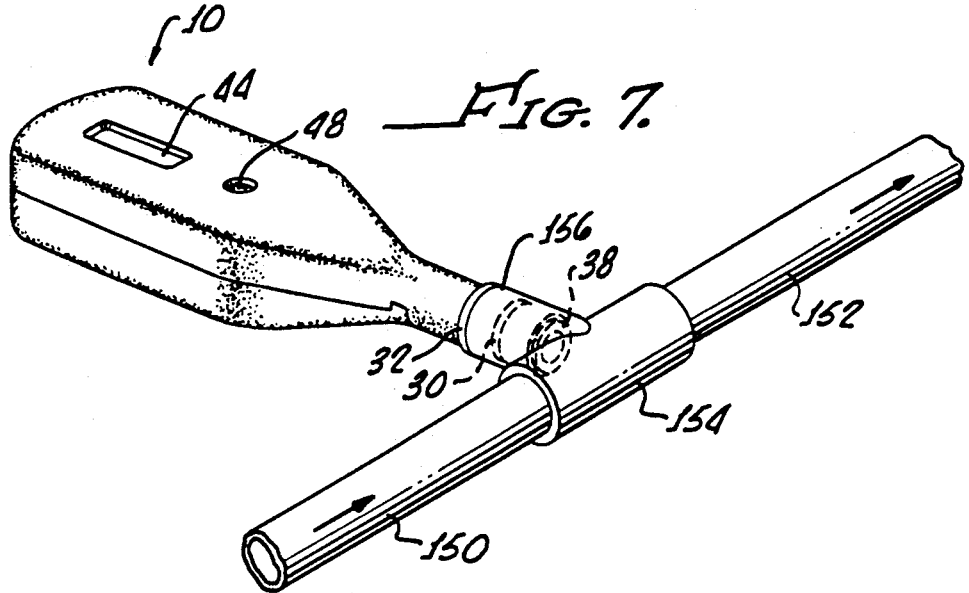

PORTABLE OXYGEN ANALYZER

BACKGROUND OF THE INVENTION

The present invention relates to oxygen sensing and more particularly concerns a small, portable self-contained instrument for secondary oxygen sensing.

In inhalation therapy a patient is provided with a controlled oxygen breathing mixture that is generally oxygen enriched air and often humidified or moisturized. The controlled oxygen breathing mixture is either provided for the interior of an enclosure or tent that surrounds the patient or is provided by inhalation therapy tubing connected between an oxygen percentage controlling device, such as for example a nebulizer or humidifier, and a breathing mask of the patient. The breathing mixture is provided for the patient by mixing ambient air with pure oxygen gas. The mixture is established and controlled by various types of oxygen control apparatus. Such apparatus may include gauges for precision reading and control of oxygen percentage and mixture flow rates and pressures or may comprise a nebulizer with built-in adjustable controls for establishing and maintaining percentage of oxygen in breathing mixtures provided to the patient.

Although breathing oxygen percentage and other components of breathing mixtures are established and maintained by primary mechanisms at the breathing mixture source, it is useful and even necessary from time to time to monitor the oxygen content of a breathing mixture actually transmitted to the patient. Thus, it is desirable for an attendant to be able to readily and conveniently monitor oxygen content at or close to the patient without adjusting or controlling remote primary oxygen sources.

Systems and apparatus presently available for gas monitoring include relatively large complex electrical devices and mechanisms, most of which are not readily portable. Some systems include a box containing monitoring and electronic circuitry connected by a long cable to a standard type of oxygen sensor. Typical of such oxygen sensors are those described in U.S. Pat. No. 4,367,133 and U.S. Pat. No. 4,077,861. The sensor generates an electrical current signal indicative of percentage of oxygen, or actually indicative of partial pressures of oxygen, and such electrical signal is transmitted to standard types of electronic circuitry for indication of oxygen content of gas being monitored. The monitoring equipment thus includes several different parts, a box or container, a sensor holder, sensor electric coupling and interconnecting cabling. Equipment of this type is relatively inconvenient to handle, store and carry. Therefore it is not readily carried about by an attendant who moves from one patient to another for various service tasks only one of which may comprise monitoring of oxygen concentration of breathing mixtures.

Accordingly, it is an object of the present invention to provide a portable oxygen sensor that avoids or minimizes above mentioned problems.

SUMMARY OF THE INVENTION

In carrying out principles of the present invention in accordance with a preferred embodiment thereof, a portable, completely self-contained oxygen analyzer includes a housing containing electrical control and display circuitry and having an integral receptacle section that receives a standard oxygen sensor capsule. The receptacle section is configured and arranged to be snugly received in a T-section fitting connected in the flow path of tubing that delivers a breathing mixture to the patient. According to a feature of the invention the entire instrument is of a size and shape to be readily received in the shirt pocket of an attendant and to be held and operated with one hand. It includes an uniquely shaped handle section of the housing and an integral receptacle section that performs the dual function of snugly receiving and electrically connecting a standard oxygen sensor cylinder and providing a connecting fitting between the sensor housing and a standard sized tubing T-section.

BRIEF DESCRIPTION OF THE DRAWINGS

FIG. 1 is an exploded perspective view of an instrument embodying principles of the invention showing a standard oxygen sensor removed from the instrument.

FIG. 2 is a plan view of an upper housing section of the instrument.

FIG. 3 is a plan view of a bottom section or cover of the housing.

FIGS. 4 and 5 are sections taken on lines 4—4 and 5—5 of FIGS. 2 and 3 respectively.

FIG. 6 is a simplified block diagram of electrical circuitry contained within the housing.

FIG. 7 illustrates application of an oxygen analyzer to a standard T-fitting placed in the upstream side of tubing that supplies a breathing mixture to the patient.

DETAILED DESCRIPTION OF A PREFERRED EMBODIMENT

As shown in FIG. an oxygen analyzer embodying principles of the present invention is a small, palm sized, hand-held and completely self-contained instrument comprising a generally rectangular hollow handle or housing section 10 having at one end a transition section 12 that tapers smoothly to a small diameter hollow tubular neck or receptacle section 14. The entire instrument has a total length less than 6¼ inches. The housing and transition sections, which form the instrument handle, and the neck section are formed of two parts, a main body part 16 that is integral with neck section 14, and a cover or auxiliary body part 18. The parts 16,18 are detachably held together by a plurality of screws (not shown in FIG. 1), with the two parts being separable from each other along a parting line generally indicated at 22 in FIG. 1. The cover part 18 ends at the beginning or inner end 19 of the neck section. The end of the cover part adjacent the neck section is formed with an interlocking projection 21 that is received in a locking recess 23 of the main body part to properly position the cover part relative to the main body part and the neck section.

The hollow tubular neck section has a forward open end 24 that slidably receives an elongated cylindrical oxygen sensor 26, which may be a standard sensor, such as the C-4 Polarographic Oxygen Sensor sold by Teledyne Industries of San Gabriel, Calif., and of the type described in U.S. Pat. No. 4,077,861, for example. The sensor has a total length, including its connecting pins, of less than two inches.

The body part 16 is formed as an injection molded elongated housing section, trough shaped in cross-section, and completely open at one side to receive the upper cover section 18. Section 18 includes a transition section 12a that tapers to its end. Body part 16 is formed with a corresponding transition portion 12b that smoothly tapers down into the integrally formed neck section 14.

Neck section 14 carries an external O-ring 30 adjacent its open end 24 and spaced from the end by a short distance. Spaced further inwardly of the O-ring and fixedly secured to and circumscribing the neck section is a rigid radially outwardly projecting stop collar 32. The neck section is symmetrically disposed relative to the main body portion from top to bottom as viewed in FIG. 1, but is offset toward the side 13 of the body portion that has the display 44. A line extending along the neck section lies substantially in the plane of side 13 so that the instrument can rest on a flat surface with side 13 of the housing and stop collar 32 of the neck section in contact with such flat surface.

The oxygen sensor 26 includes a sealing O-ring 36 adjacent a sensor end 38 thereof, and, at its other end, carries a plurality of connector pins 40 (there being three in a typical sensor) which are arranged to be received in a suitably configured socket or connector receptacle 66 (FIG. 2) that is carried at an inner portion of neck section 14. A display screen 44 is mounted on a circuit board 50 (FIG. 2) within the housing to be viewed through a display opening in side 13 of the body part 16. The latter also has an aperture 46 formed therein through which access can be had to a calibration adjustment knob 48 carried on the circuit board 50 that is mounted in main body part 16.

As can be seen in FIG. 2, body portion 16 fixedly carries an elongated circuit board 50 having a configuration roughly the same as that of the body portion 16. Conveniently the circuit board 50 is fixedly secured to and within the body portion by means of adhesive, such as epoxy adhesive at areas 52. The circuit board carries an on/off switch 54 operable by a switch button 56 which is connected to the switch and projects outwardly through an end 58 of the body portion. A first calibration adjustment screw 60 is mounted on the circuit board and is accessible through a hole 62 (FIG. 3) in the cover portion of the analyzer housing. The circuit board, being configured to mate with the configuration of the tapering body part 16 has an end portion 64 to which is mounted the connector receptacle 66 having a plurality of sockets configured and arranged to receive and electrically contact pins 40 on the end of the oxygen sensor when the latter is slidably inserted into the neck section of the housing.

FIG. 3 is a plan view of the inner side of the cover portion. The latter includes a depressed platform 70 formed with two partly circular wells 72,74 in which are mounted two batteries 73 (FIG. 5) for powering the electrical portions of the apparatus. An audio speaker or buzzer 76 fixedly mounted to the inside of the cover portion 18 is connected by flexible folded leads generally indicated at 78 to the circuit board 50. Power lines 82 connect the batteries to the circuit board. A hole 86 in the cover portion 18 allows access by means of a small tool to an operator 88 of a polarizer switch 89 (FIG. 4) mounted on the circuit board.

The cover part is detachably fixed to the body part by several screws. A plurality of apertures 90a,90b,90c,90d, and 90e in cover part 18 receive headed screws (not shown) that are threadedly engaged in suitable apertures 92a,92b,92c,92d and 92e formed through the circuit board and threaded in the body portion 16 of the housing. The outer surface of cover part 18 mounts a removable battery section cover 96 (FIG. 5) that permits access to the batteries.

FIG. 6 is a simplified block diagram of the circuitry contained within the handle formed by the housing and transition sections 10 and 12. Depression of start button 56 operates start switch 54 to send a start signal to a system timing and control circuit 100. The timing circuit for the sensing operation provides for two immediately adjoining ten second periods, the first of which is a sense or capture period that is immediately followed by a reading period. During the ten second capture period the sensor is caused to read oxygen percentage (actually partial pressures) and to display this percentage on a liquid crystal display (LCD) 44 that is driven by an analog to digital converter and display driver 102. The converter and display driver receives a voltage on a line 104 that has a value which is a function of the percent of oxygen read by the oxygen sensor 26. The latter is connected by its pins 40 to a sensor interface circuit 106 that forms part of the system electronics. System timing during the ten second sense period sends a signal on lines 110,112 to activate the sensor interface and the display driver so that the display will read a changing percentage during this ten second sense period as the sensor reading settles to a fixed amount. At the end of the ten second sense period, the signals from the system timing via lines 110 and 112 are removed and a second ten second enabling signal is fed to the analog to digital converter and display driver 102 via a line 114. Continued transmission of values sensed by the sensor is stopped during the read period. This causes the liquid crystal display (LCD) 44 to show the last value of the sensed oxygen content that was determined during the ten second sensing period. During the ten second reading period the timing system sends a signal via a line 116 to buzzer 118 which continuously emits an audible signal during the ten second reading period to alert the operator to read the display. During this read period line 114 also sends a signal via a line 120 to a fiber optic back light 132 for illuminating display 44. A polarization button 88 operates polarization switch 89 that sends a signal via a line 136 to the system timing and control circuit 100 for polarization of the oxygen sensor in a conventional manner. For polarization a 1.5 volt signal of about fifteen seconds duration, positive relative to the sensor anode, is applied. Batteries indicated as a power supply 140 feed power through a low battery detection circuit 142 to system timing and control circuit 100. When a low battery is detected a low battery enable signal on line 144 is transmitted to the system timing and control circuit which feeds a signal on a line 146 to the LCD display to alert the operator to the low voltage of the battery.

The described oxygen analyzer is employed simply by introducing the gas to be analyzed to the front end 38 of the oxygen sensor after the latter has been inserted into the neck section of the apparatus. Pressing start button 56 starts the apparatus, which immediately goes into its sensing mode for ten seconds, during which period the sensor is producing a signal representing the percentage of oxygen in the ambient gas. As previously mentioned, at the end of this ten second period, during which the display reading may vary, a reading period starts. The reading period is signaled by the audible tone of the buzzer. The buzzer continues during the entire ten second reading period, during which period the display value remains fixed at the value sensed at the end of the sensing period.

As previously mentioned, the disclosed instrument is a convenient secondary monitoring device. It is not designed for use as a primary device for use in initially establishing or controlling the oxygen content of the mixture. The device is conveniently used to check on the oxygen content of an inhalation or respiratory therapy breathing mixture that is transmitted from a breathing mixture source (not shown) via a therapy tube section 150 (FIG. 7) to a patient (not shown) via a downstream section of tubing 152. A standard "T" fitting 154 is inserted in the tubing section at a position upstream of the patient. The oxygen sensor is inserted into the analyzer neck section 14, as previously described, and an end of the neck section together with the oxygen sensor are then inserted in the T leg 156 of the T-fitting 154 to expose the oxygen sensor to the gas inhalation mixture being fed to the patient. Stop collar 32 prevents insertion of the analyzer too far into the fitting leg 156, where it might obstruct flow through tubing 150,152. The analyzer is then operated as previously described simply by pressing the start button, waiting the ten second sensing period and then noting the oxygen percentage during the audibly signalled reading period.

Initially, for use of a new analyzer, the sensor is activated or polarized by pressing the switch 88,89 (FIGS. 2,4) located at the bottom of hole 86 (FIG. 3). A small screwdriver or paper clip may be employed. This will activate the sensor and thereafter requires a twelve hour period to allow the sensor to stabilize after this initial polarization.

For a first step in calibration of the apparatus the analyzer is positioned in fresh ventilated room air and the on button 56 pressed. The analyzer initially senses room air concentration for ten seconds, as may be observed by the changing digital display on the screen. Following the ten second sensing period, system timing holds the display on the screen at a fixed value for a ten second read period, during which the buzzer sounds to alert the operator. At the end of this ten second read period the display is automatically extinguished by system timing, the buzzer ceases sounding and the analyzer circuit automatically turns itself off. During this reading period, for calibration, a small flat screwdriver is placed into the calibrating hole 62 (FIG. 3) to turn adjustment control 60 and vary the digital readout until a reading of 21% is attained on the display screen. Such an adjustment is made only during the sensing period. This adjustment varies signal offset. This adjustment may be checked by allowing another full ten second sensing period to occur without adjustment to make sure that there is a 21% reading.

As a second step for the calibration the analyzer sensor is placed in a dry 100% oxygen supply, which may be performed by inserting the oxygen sensor into a leg of a T supplied with 100% dry oxygen. Preferably oxygen flow rate should be between two and ten liters per minutes, with oxygen pressure maintained at a level similar to the pressure of the gas to be analyzed. In any event the oxygen pressure should be no greater that 150 cm of water pressure. Now the 100% calibrating recess knob 48 (FIG. 1) is adjusted until the digital readout reads 100%. Again, adjustments should be made only during the sensing period. When a constant 100% reading has been achieved, the adjustment may be checked by allowing a full sensing period without adjustment to yield a 100% read period during this second step.

A third step in the calibration is to place the analyzer again into the fresh ventilated air, wait for thirty seconds and check the oxygen concentration to be sure that it is within the range of 19% to 23%. If this range does not show on the display, readjustment of the 21% calibration, as in the first mentioned step, should be carried out. This last step of checking oxygen concentration may be repeated for accuracy.

To maintain maximum accuracy, the analyzer is preferably calibrated prior to each use, or at least every eight hours. It is not necessary to polarize the sensor for each calibration. When inserting the neck section into the leg of the T-fitting, the O-ring 30 seals the neck section to prevent gas leakage from the circuit, and the stop collar 32 prevents the sensor from penetrating too far into the circuit and thereby restricting flow through the tubing.

In an exemplary embodiment the entire apparatus is a unitary self-contained, rigid, molded, two-part plastic housing that is readily carried in an operator's shirt pocket and is readily held in the palm of the operator's hand. Only one hand is needed to both hold and operate the device. The total length of the housing and neck section is about 6⅛ inches. A cross-section of the handle part of the housing is about 1⅝ inches wide by ⅞ inches thick. The outside diameter of the neck section is about ½ inch, and it has a length slightly greater than the overall 1¼ inch length of the standard oxygen sensor. The described size and shape of the oxygen analyzer disclosed herein greatly improves the convenience of use and handling. Rather than carrying around bulky equipment having movable parts and elongated cables, the entire instrument of the present invention may be readily carried in a shirt pocket and held and used while in the palm of one hand. The housing section, because of its size and shape, actually performs two functions, namely (a) mounting and containing the electrical circuitry, display and controls, and (b) serving as a handle for manipulating the receptacle section and sensor for insertion into a T-fitting.

The neck section 14 also performs a dual function. First is forms a connector fitting for coupling the analyzer with a T-fitting. In addition it forms a receptacle for mounting the oxygen sensor both physically and electrically.

Although the neck section extends in the direction of the long axis of the rectangular handle section, the described integral palm sized instrument may have other configurations. For example, the instrument may be "T" shaped, with the neck section extending from a mid-section of the handle section perpendicular to the long axis of the handle, or the entire device may be "L" shaped, with the neck section extending from an end of the handle section perpendicular to the long axis.

The foregoing detailed description is to be clearly understood as given by way of illustration and example only, the spirit and scope of this invention being limited solely by the appended claims.

What is claimed is:

1. In combination with patient breathing therapy apparatus including a therapy tube for transmitting a respiratory therapy breathing mixture to a patient, and a "T" fitting in said therapy tube adjacent a patient and having first and second legs connected to said tube and a third connecting leg, a self-contained, palm size, hand held secondary oxygen monitoring device, said self-contained monitoring device being configured and arranged to be held in one hand and to be inserted into and removed from said "T" fitting by manipulation with a single hand, to enable monitoring of the oxygen content of the breathing mixture adjacent a patient, said monitoring device comprising:

a generally rectangular housing having an elongated body section adapted to fit the palm of a hand, an elongated tubular neck forming an oxygen sensor receptacle section of relatively small diameter, said neck having a free outer end slidably insertable into and removably received within said third connecting leg of said "T" fitting, said body section having a thickness and width greater than said sensor receptacle section diameter, a housing transition section integral with both said body section and tubular neck, said housing transition section being smoothly tapered from a first portion thereof adjacent said body section that has a configuration and dimensions of said body section to a second portion thereof adjacent said neck that has a configuration and dimensions of said neck, electrical control and display circuitry mounted within said body section, said circuitry including a circuit board having a tapered section in said housing transition section, having an end positioned at an inner end of said tubular neck, a socket means on said end of said circuit board tapered section, said housing being configured and arranged to form a handle for the monitoring device and to provide a mounting an enclosure for said electrical control and display circuitry, and an elongated tubular oxygen sensor slidably inserted into and received within said sensor receptacle section and having a plurality of contact pins received in said socket means, whereby said tubular neck forms a connector fitting for connecting the monitoring device to said "T" fitting.

2. The combination of claim 1 wherein said housing comprises a body part and a cover part detachably secured thereto, said elongated tubular neck comprising a unitary, integral and circumferentially continuous elongated cylinder, said body part including a portion of said body section and said circumferentially continuous cylinder and having a transition portion that tapers to said tubular neck, said cover part having an end adjacent said neck, an interlocking projection on said cover part end, a recess formed in said body part adjacent said cover part end and receiving said interlocking projecting to properly position said cover part relative to said body part and tubular neck.

3. The combination of claim 1 wherein said circuitry includes timing means for establishing a reading time interval and a sensing time interval preceding said reading time interval, means responsive to said oxygen sensor during said sensing time interval for reading values of varying oxygen percentage, and means operable during the reading time interval for displaying the last value of oxygen percentage read during the sensing interval.

4. The combination of claim 1 wherein said circuitry includes a sensing time circuit means for establishing a sense time, and read time circuit means for establishing a read time following said sense time.

5. The combination of claim 4 including means for audibly signaling the end of said sense time.

6. The combination of claim 4 including means for audibly signaling said read time.

7. The combination of claim 5 wherein said circuit means includes means for turning on said circuit means to initiate operation of said sense and read times, and means for turning off said circuit means at the end of said read time.

* * * * *